(12) United States Patent
Kopp et al.

(10) Patent No.: US 6,177,494 B1
(45) Date of Patent: Jan. 23, 2001

(54) N,N'-DISUBSTITUTED N-(2-HYDROXYALKYL)-UREAS

(75) Inventors: Richard Kopp, Köln; James-Michael Barnes, Hochscheid; Hans-Dieter Ruprecht, Köln; Hans-Georg Wussow, Düsseldorf, all of (DE)

(73) Assignee: Bayer Aktiengesellschaft, Leverkusen (DE)

( * ) Notice: Under 35 U.S.C. 154(b), the term of this patent shall be extended for 0 days.

(21) Appl. No.: 09/366,527

(22) Filed: Aug. 2, 1999

(30) Foreign Application Priority Data

Aug. 7, 1998 (DE) ................................ 198 35 703

(51) Int. Cl.⁷ ................ C08J 3/00; C08K 5/21; C08L 75/00; C08G 18/81; C07D 273/04
(52) U.S. Cl. ............... 524/212; 524/589; 524/590; 528/44; 528/45; 528/73; 528/85; 544/1; 544/63; 544/68; 560/330; 560/332
(58) Field of Search .................... 524/589, 590, 524/212; 528/44, 45, 73, 85; 560/330, 332; 544/1, 63, 68

(56) References Cited

U.S. PATENT DOCUMENTS

| 3,795,638 | 3/1974 | Grögler ............... 260/45.9 R |
| 4,757,105 | * 7/1988 | Kopp et al. ............... 524/714 |

FOREIGN PATENT DOCUMENTS 2200823   9/1997   (CA) .

* cited by examiner

Primary Examiner—Patrick D. Niland
(74) Attorney, Agent, or Firm—Joseph C. Gil; Lyndanne M. Whalen

(57) ABSTRACT

Non-crystallizing N,N'-disubstituted N-(2-hydroxyalkyl)-ureas are used as hydrolysis protection agents in plastics containing ester groups. These disubstituted hydroxyalkylureas impart excellent protection from hydrolysis to plastics containing ester groups and can be added directly to the plastics to be stabilized without the addition of special solvents.

4 Claims, No Drawings

N,N'-DISUBSTITUTED N-(2-HYDROXYALKYL)-UREAS

BACKGROUND OF THE INVENTION

The present patent application relates to non-crystallizing N,N'-disubstituted N-(2-hydroxyalkyl)-ureas and to the use thereof as hydrolysis protection agents in plastics which contain ester groups.

N,N'-disubstituted N-(2-hydroxyalkyl)-ureas or -thioureas which are used as hydrolysis protection agents for plastics that contain ester groups are disclosed in DE-A 2,106,726. One disadvantage of the ureas or thioureas which are described in this German Patent is their crystallinity, which makes it difficult to admix these ureas in a homogeneous form with plastics containing ester groups and to stabilize such mixtures. These disclosed ureas therefore have to be melted before processing which constitutes an additional operating step. This additional operating step and the crystallinity of these hydrolysis protection agents adversely affect the economics of using the ureas or thioureas described in German Patent 2,106,726 to stabilize plastics which contain ester groups.

Another disadvantage of using the ureas or thioureas described in German Patent 2,106,726 is thermal cleavage due to overheating caused, e.g., by incorrect processing during attempts to liquefy them before they are admixed with the plastics containing ester groups, which liquefaction step is often carried out at considerably increased oven temperatures. Thermal cleavage results in the formation of volatile iso(thio)cyanates which constitute a physiological risk to the processing operator. Over-heating can also occur when these known ureas are used in systems in which curing is conducted at elevated temperatures, e.g., during the processing of thermoplastics using continuous screw devices or during the cure of cast elastomers.

SUMMARY OF THE INVENTION

It is an object of the present invention to provide non-crystallizing ureas.

It is also an object of the present invention to provide hydrolysis protection agents for plastics containing ester groups.

These and other objects which will be apparent to those skilled in the art are accomplished by producing N,N'-disubstituted N-(2-hydroxy-alkyl)-ureas from trimerized hexamethylene diisocyanate and incorporating such ureas into plastics containing ester groups.

DETAILED DESCRIPTION OF THE PRESENT INVENTION

It has now been found that when trimerized hexamethylene diisocyanate is used as a starting material for the production of N,N-disubstituted N-(2-hydroxyalkyl)-ureas, non-crystallizing products are obtained. These non-crystallizing products can be used without problems, optionally as stable solutions in 1,4-butanediol, and impart excellent protection from hydrolysis to plastics containing ester groups.

The present invention therefore relates to non-crystallizing N,N'-disubstituted N-(2-hydroxyalkyl)-ureas represented by general Formula (I)

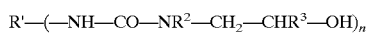

in which $R^1$ represents the radical of a trimerized hexamethylene diisocyanate which is diminished by the loss of free NCO groups, $R^2$ represents an aliphatic or aromatic hydrocarbon radical having up to 18 carbon atoms, which is optionally substituted by hydroxyl or cyano groups or by one or more halogen atoms, $R^3$ represents hydrogen or an alkyl radical having from 1 to 12 carbon atoms, preferably from 1 to 3 carbon atoms, and n on average, represents a number from 3.0 to 5.0, preferably from 3.2 to 4.5.

The preferred N,N'-disubstituted N-(2-hydroxyalkyl)-ureas of general Formula (I) are those in which n represents 3.2 to 4.5, $R^2$ represents a methyl or hydroxyethyl group, $R^3$ represents hydrogen or a methyl group, and $R^1$ represents a radical of a trimerized hexamethylene diisocyanate, which is diminished by the loss of free NCO groups, corresponding to the idealized Formula (II):

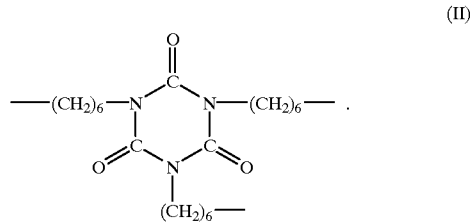

The expression "idealized form of trimerized hexamethylene diisocyanate" refers to the fact that oligomers made up of trimers linked by hexamethylene bridges are also formed during the production of trimerized hexamethylene diisocyanate. Furthermore, the compounds can also contain what are termed asymmetric trimer rings of the following Formula (III)

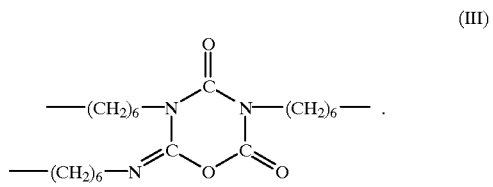

Production of trimers having an increased proportion of these asymmetric trimer rings is described, for example, in DE-A 1,961,1849.

The non-crystallizing N-alkyl-N-2-hydroxyalkyl-ureas corresponding to Formula (I) according to the invention may be produced by known methods of preparative organic chemistry such as addition of N-substituted 2-hydroxyalkylamines to trimerized hexamethylene diisocyanate at reaction temperatures of from 20 to 1 00° C., preferably from 20 to 70° C.

This addition reaction may be conducted either in solution or in bulk, but is preferably conducted in solution. Suitable solvents are those which do not have a negative effect on the use of the ureas according to the invention as hydrolysis protection agents in plastics, such as customary plasticizers (e.g., dioctyl phthalate), or organic solvents such as ethanol, isopropanol, dioxane, tetrahydrofuran, chloroform and/or 1,4-butanediol.

To remove subsidiary components of the N-substituted 2-hydroxy-alkylamines, which subsidiary components do not react or which only react slowly with isocyanate groups (e.g., N,N-dimethylaminoethanol, N,N-diethylaminoethanol or trimethylamine), the reaction product from the addition reaction, or a solution of the reaction product, can be subjected to a brief vacuum treatment, wherein a gentle flow of nitrogen can be passed through the batch to promote volatilization.

The starting materials, namely the substituted hydroxylamines and the trimerized hexamethylene diisocyanate, are generally used in an equivalent ratio of isocyanate groups to NH groups offrom 1:1 to 1.1:1, preferably from 1:1 to 1.05:1.

As mentioned above, trimerized hexamethylene diisocyanate is used as the isocyanate starting material for the production of ureas of general Formula (I) according to the invention. This isocyanate is obtained by the partial trimerization of hexamethylene diisocyanate and subsequent removal of unreacted monomeric hexamethylene diisocyanate. The production of trimerized hexamethylene diisocyanate is described, for example, in J. Prakt. Chem. 336 (1994) 185–200 and in EP-A 339,396 and EP-A 798,299. These isocyanates are obtainable as commercial products, under trade names such as Desmodur® N 3300 and VP® LS 2025/1, from Bayer AG, Leverkusen.

Suitable reactants for the trimerized hexamethylene diisocyanate include any N-substituted 2-hydroxylalkylamines, preferably 2-hydroxy-ethylamines, such as N-meth-yl-2-hydroxyethylamine, N-methyl-2-hydroxybutylamine, N-isopropyl-2-hydroxy-ethylamine, N-butyl-2-hydroxyhexylamine, or bis(2-hydroxyethyl)-amine.

N-methyl-2-(hydroxyethyl)amine is most preferably used. N-substituted 2-hydroxyl-alkylamines are also described in the above-mentioned German Patent 2,106,726.

The present invention further relates to the use of the non-crystallizing N-alkyl-N-2-hydroxyalkyl-ureas of general Formula (I) to stabilize (as hydrolysis protection agents) any plastics, preferably polyurethanes, which contain ester groups.

In general, from 0.02 to 10% by weight, preferably from 0.1 to 5% by weight, of the hydrolysis protection agent of the present invention is sufficient to stabilize plastics containing ester groups. The hydrolysis protection agents used in the practice of the present invention can either be added to the plastics to be stabilized after the production thereof, or be admixed with the starting materials from which the plastics containing ester groups are produced. The latter type of addition is recommended, particularly for polyurethanes with stabilized ester groups. If the hydrolysis protection agent of the present invention is added during production of a polyurethane, the hydrolysis protection agent can be added either to the polyisocyanate component or to the polyol component.

The expression "polyurethanes which contain ester groups" means any polyurethanes which are produced from hydroxyl compounds containing ester groups, e.g., polyurethane (integrally) foamed materials, polyurethane elastomers, thermoplastic polyurethanes (TPUs), polyurethane fibers and polyurethane coating media.

In addition to their suitability for stabilizing polyurethane plastics containing ester groups, the ureas of general Formula (I) are also suitable for stabilizing any other plastics containing ester groups, such as polyesters that are formed from dibasic dicarboxylic acids (e.g., phthalic acid, terephthalic acid or adipic acid) and polyhydric alcohols such as ethylene glycol, hexanediol, glycerol, trimethylpropane and pentaerythritol. Other plastics which can be stabilized with the ureas corresponding to Formula (I) include polymers or copolymers containing lateral ester groups that are based on esters of acrylic acid or of methacrylic acid, and on vinyl esters such as polyvinyl acetate. Plastics of this type may exist, for example, as lacquers, films, coatings, fibers, foamed materials, elastomers, casting resins or as pressed bodies.

The following Examples are given to illustrate the present invention. All parts and percentages given in these Examples are parts by weight or percentages by weight, unless otherwise indicated.

EXAMPLES

Example 1

N-methyl-ethanolamine (N-MEA) was reacted with hexamethylene-1,6-diisocyanate (HDI) and trimerized hexamethylene diisocyanate (which is commercially available under the name Desmodur N 3300) in iso-propanol.

N-methyl-N-hydroxyethylureas based on HDI and based on trimerized HDI (Desmodur N 3300) were prepared in isopropanol and the properties of the solutions and of the isolated ureas were subsequently determined. These properties are reported in the following Table:

| Test | Isocyanate | NCO content [% by weight] | Amount used [g] | Equiv. NCO | Amount of N—MEA [g] | Equiv. NH | NCO:NH index |
|---|---|---|---|---|---|---|---|
| a | HDI | 49.98 | 60.00 | 0.71 | 53.60 | 0.71 | 1.00 |
| b | N 3300[a] | 21.30 | 68.97 | 0.35 | 26.30 | 0.35 | 1.00 |

N 3300[a]: Desmodur ® N 3300, Bayer AG, Leverkusen

Experimental 100 parts by weight of isopropanol were introduced with stirring, together with the amount of N-methyl-ethanolamine indicated in the Table above, into a 250 ml three-necked flask. The isocyanate component, which was heated to 40° C., was added drop-wise with stirring. The reaction temperature was limited to 50° C. by applying slight cooling.

After the drop-wise addition was complete, the batch was stirred further until the typical band of the isocyanate group at about 2250 cm$^{-1}$ was no longer visible in the infrared (IR) spectrum.

Results:

In test a, a solution was obtained which was initially homogeneous at 50° C., but which spontaneously and suddenly crystallized out after it had cooled and was allowed to stand at room temperature. In test b, a clear solution was obtained which had a viscosity of 390 mPa·s at 25° C. This solution did not change when it was allowed to stand for a longer period.

A portion of each product obtained was carefully evaporated in a rotary evaporator, under vacuum from a water pump. White crystals with a melting point of about 97° C. (Kofler bank) were obtained from the product of test a; a viscous liquid which did not crystallize out even when cooled to 0° C. was obtained as the product of test b.

Example 2

N-methyl-ethanolamine (N-MEA) was reacted with hexamethylene-1,6-diisocyanate (HDI) and trimerized hexamethylene diisocyanate (Desmodur N 3300) in 1,4-butanediol.

The amounts of isocyanate and N-MEA used are reported in the table below. These amounts were selected so that both products contained the same concentration of N-methyl-N-hydroxyethyl groups which were definitive for protection from hydrolysis, calculated as the N-MEA content.

Example 3

The effectiveness of the hydrolysis stabilizers of the present invention in PUR casting systems was determined.

Example 3a (Comparative Example, Unstabilized)

1000 g (0.5 mole) of a commercially available polyethylene adipate having an average molecular weight of 2000 were heated to 125° C. and mixed with 180 g (1.714 moles) of naphthalene 1,5-diisocyanate. The mixture was immediately stirred intensively and after 2 minutes was degassed under vacuum. An NCO prepolymer was formed after about 15 minutes by an exothermic reaction. 20 g (0.222 mole) of 1,4-butanediol were stirred as a crosslinking agent into this prepolymer. The reacting mixture was cast within 1 minute into molds which had been preheated to 110° C., and

| Test | Iso-cyanate | NCO content [% by weight] | Amount used [g] | Equiv. NCO | Amount N—MEA [g] | Equiv. NH | Amount 1,4-butane-diol [g] | NCO:NH index | N—MEA content [% by weight] |
|---|---|---|---|---|---|---|---|---|---|
| a | HDI | 49.98 | 207.40 | 2.47 | 176.40 | 2.35 | 575.00 | 1.05 | 18.40 |
| b | N 3300 | 21.63 | 476.34 | 2.45 | 175.44 | 2.34 | 301.92 | 1.05 | 18.40 |

Experimental 1,4-butanediol and N-methyl-ethanolamine were introduced with stirring into a 2 liter three-necked flask. The isocyanate component, which was heated to 40° C., was added drop-wise with stirring and the reaction temperature was limited to about 50° C. by applying slight cooling.

After the drop-wise addition was complete, the batch was stirred further until the typical band of the isocyanate group at about 2250 cm$^{-1}$ was no longer visible in the IR spectrum.
Results:

In test a, a clear homogeneous solution was initially obtained but crystals gradually formed as the solution was cooled to room temperature. After some time at room temperature, the mixture had crystallized almost completely throughout. The crystal-line paste could be re-melted by heating it to 50 to 55° C.

In test b, a homogeneous solution was obtained which had a viscosity of 3340 mPa·s at 25° C. This solution was still free-flowing when cooled to 0° C., and showed no tendency to crystallize.

solidified therein after a few minutes. The resulting elastomer was post-annealed for 24 hours at 110° C. and was subsequently stored for 4 weeks at room temperature.

An elastomer which had the properties listed in Table 1 was obtained. The susceptibility to hydrolysis of this elastomer is documented in Table 1.

Example 3b
(according to the invention)

A prepolymer was produced analogously to that produced in comparative Example 3a with the exception that a mixture of 1,4-butanediol (16.1 g) and the solution of hydrolysis protection agent (12.5 g) which contained 1,4-butanediol prepared in accordance with Example 2b was used as the crosslinking agent. The resulting elastomer was post-annealed for 24 hours at 110° C. and was subsequently stored for 4 weeks at room temperature.

An elastomer was obtained which had the properties listed in Table 1. The improved resistance to hydrolysis of this elastomer compared with that of Example 3a is also documented in Table 1.

TABLE 1

| Physical properties | | DIN/ISO | Example 3a (comparative) | Example 3b (according to the invention) |
|---|---|---|---|---|
| Stress at 100% strain | (MPa) | 53504/37 | 4.3 | 4.2 |
| Stress 4 300% strain | (MPa) | 53504/37 | 7.8 | 7.5 |
| Tensile strength | (MPa) | 53504/37 | 49 | 39 |
| Elongation at break | (%) | 53504/37 | 663 | 632 |
| Tear propagation resistance | (kn./m) | 53515/34 | 31 | 27 |
| Rebound resilience | (%) | 53512/4662 | 60 | 61 |
| Abrasion loss | (mm$^3$) | 53516/4649 | 37 | 51 |
| Compression set | | 53517/815–1991 | 18 | 26 |
| 70 hours at 23° C. | (%) | | | |
| Properties after aging for 11 days in water at 80° C. | | | | |
| Stress at 100% strain | (MPa) | 53504/37 | destroyed | 2.7 |
| Stress at 300% strain | (MPa) | 53504/37 | — | 4.3 |

TABLE 1-continued

| Physical properties | | DIN/ISO | Example 3a (comparative) | Example 3b (according to the invention) |
|---|---|---|---|---|
| Tensile strength | (MPa) | 53504/37 | — | 16.4 |
| Elongation at break | (%) | 53504/37 | — | 1082 |

Formulations:

| | Test | | | | | | |
|---|---|---|---|---|---|---|---|
| | a | b | c | d | e | f | g |
| PE 225 B[a] | 100.0 | 100.0 | 100.0 | 100.0 | 100.0 | 100.0 | 100.0 |
| 1,4-butanediol | 10.5 | 10.5 | 10.5 | 10.5 | 10.5 | 10.5 | 10.5 |
| Loxamid EBS[b] | 0.5 | 0.5 | 0.5 | 0.5 | 0.5 | 0.5 | 0.5 |
| Stabaxol 1[c] | — | 0.4 | 0.8 | — | — | — | — |
| Stabaxol P 200[d] | — | — | — | 0.4 | 0.8 | — | — |
| Example 2b | — | — | — | — | — | 0.4 | 0.8 |
| | | comparative | | | | according to the invention | |

MDI Index: 1.01

Starting materials:

PE 225 B[a]: a polyester of adipic acid and 1,4-butanediol, molecular weight 2250, OH number 50

Loxamid EBS[b]: a wax produced by Henkel KGaA

Stabaxol 1[c]: a hydrolysis stabilizer of the carbodiimide type, produced by Rheinchemie, Mannheim Stabaxol P 200[d]: a hydrolysis stabilizer of the carbodiimide type, produced by Rheinchemie, Mannheim.

Casting tests:

Casting tests were performed by the one-shot method. The ester was allowed to react with Stabaxol 1, Stabaxol P 200 or the product from Example 2b overnight.

After mixing the ester containing the stabilizer with Loxamid EBS and 1,4-butane-diol, the temperature was brought to 140° C. by means of a gas heater. Thereafter, the MDI was added with stirring (it was stirred in for about 30 seconds).

The reaction product was then cast onto a metal sheet which had been preheated to 80° C. and was allowed to stand for 5 minutes. It was reheated to 80° C. for 30 minutes in a drying oven and was subsequently allowed to cool overnight. The slabs were then cut and granulated.

Processing:

The granular mixtures were dried and then injection-molded in a Mannesmann-Demag Type D60 injection-molding machine to form test specimens. The injection-molded bodies were annealed before testing.

Within the scope of the accuracy of measurement, the stabilizer from Example 2 (produced in accordance with the invention) exhibited an efficacy comparable to that of commercially available stabilizers of the carbodiimide type.

TABLE 2

| | Test | | | | | | |
|---|---|---|---|---|---|---|---|
| Stabilizer | a None | b Stabaxol 1 | c | d Stabaxol P 200 | e | f Compound from Example 2b | g |
| Properties before aging | | | | | | | |
| 100% Stress N/mm²) | 5.9 | 5.8 | 5.8 | 5.8 | 5.5 | 6.1 | 5.6 |
| 300% Stress (N/mm²) | 15.2 | 16.6 | 15.3 | 16.9 | 15.0 | 17.2 | 14.8 |
| Tensile strength (N/mm²) | 58.4 | 50.5 | 52.1 | 54.6 | 53.5 | 54.6 | 56.3 |
| Elongation at break (%) | 540 | 507 | 553 | 515 | 539 | 508 | 562 |
| Young's modulus in tension | 17.4 | 16.2 | 20.0 | 18.7 | 12.5 | 17.3 | 18.3 |
| Properties after 7 days | | | | | | | |
| 100% Stress (N/mm²) | 5.0 | 5.3 | 5.4 | 5.3 | 5.5 | 5.6 | 5.2 |
| 300% Stress (N/mm²) | 12.1 | 13.7 | 13.4 | 14.3 | 15.1 | 15.2 | 13.2 |
| Tensile strength (N/mm²) | 49.3 | 47.9 | 50.1 | 50.2 | 49.3 | 48.0 | 52.1 |
| Elongation at break (%) | 630 | 533 | 547 | 525 | 519 | 515 | 602 |
| Young's modulus in tension | 14.8 | 16.2 | 17.4 | 13.5 | 14.7 | 16.1 | 19.7 |
| Properties after 14 days | | | | | | | |
| 100% Stress (N/mm²) | 4.1 | 5.2 | 4.8 | 4.8 | 5.0 | 5.1 | 4.9 |
| 300% Stress (N/mm²) | 8.3 | 13.3 | 12.3 | 12.6 | 13.5 | 13.6 | 12.3 |
| Tensile strength (N/mm²) | 19.1 | 49.5 | 46.7 | 47.9 | 49.7 | 47.0 | 47.2 |
| Elongation at break (%) | 652 | 650 | 590 | 577 | 442 | 561 | 626 |
| Young's modulus in tension | 13.7 | 14.8 | 18.6 | 16.1 | 18.8 | 12.5 | 16.1 |
| Properties after 21 days | | | | | | | |
| 100% Stress (N/mm²) | — | 4.9 | 4.8 | 4.7 | 5.0 | 5.1 | 4.8 |
| 300% Stress (N/mm²) | — | 12.5 | 11.5 | 11.5 | 13.3 | 13.2 | 11.9 |
| Tensile strength (N/mm²) | 1.7 | 45.3 | 42.5 | 41.0 | 44.1 | 42.5 | 46.0 |
| Elongation at break (%) | 25.5 | 560 | 600 | 626 | 528 | 548 | 622 |
| Young's modulus in tension | 10.0 | 14.8 | 13.5 | 11.3 | 12.5 | 16.6 | 16.1 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A non-crystallizing N,N'-disubstituted N-(2-hydroxyalkyl)-urea represented by the general Formula (I)

$$R^1\text{—}(\text{—NH—CO—NR}^2\text{—CH}_2\text{—CHR}^3\text{—OH})_n \qquad (I),$$

in which $R^1$ represents the radical of a trimerized hexamethylene diisocyanate which is diminished by the loss of free NCO groups, $R^2$ represents an aliphatic or aromatic hydrocarbon radical having up to 18 carbon atoms, which is optionally substituted by hydroxyl or cyano groups or by a halogen atom, $R^3$ represents hydrogen or an alkyl radical having from 1 to 12 carbon atoms, and n on average represents a number from 3.0 to 5.0.

2. The N-alkyl-N-2-hydroxyalkyl-urea of claim 1 in which in Formula (I), n represents 3.2 to 4.5, $R^2$ represents a methyl or hydroxyethyl group, $R^3$ represents hydrogen or a methyl group, and $R^1$ represents a radical of a trimerized hexamethylene diisocyanate, which is diminished by the loss of the free NCO groups having the idealized Formula (II):

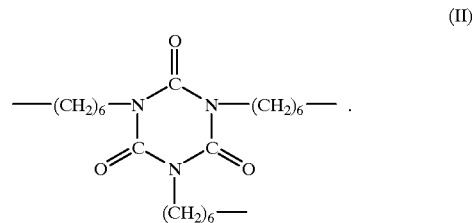

3. A method for protecting plastics containing ester groups from hydrolysis comprising adding the urea of claim 1 to the plastic.

4. A method for protecting polyurethanes containing ester groups comprising adding the urea of claim 1 to the polyurethane.

* * * * *